US008757805B2

(12) United States Patent
Hytowitz

(10) Patent No.: US 8,757,805 B2
(45) Date of Patent: Jun. 24, 2014

(54) ANIMATED IMAGE VISION TEST

(76) Inventor: Allan N. Hytowitz, Alpharetta, GA (US)

( * ) Notice: Subject to any disclaimer, the term of this patent is extended or adjusted under 35 U.S.C. 154(b) by 109 days.

(21) Appl. No.: 13/337,277

(22) Filed: Dec. 26, 2011

(65) Prior Publication Data

US 2012/0327369 A1 Dec. 27, 2012

Related U.S. Application Data

(63) Continuation-in-part of application No. 12/583,225, filed on Aug. 17, 2009, now Pat. No. 8,083,353.

(51) Int. Cl.
*A61B 3/02* (2006.01)
*A61B 3/032* (2006.01)

(52) U.S. Cl.
CPC ...................................... *A61B 3/032* (2013.01)
USPC ........................................................ 351/239

(58) Field of Classification Search
USPC ........................................................ 351/239
See application file for complete search history.

(56) References Cited

U.S. PATENT DOCUMENTS 8,083,353 B2 * 12/2011 Hytowitz ...................... 351/239

* cited by examiner

*Primary Examiner* — Jack Dinh
(74) *Attorney, Agent, or Firm* — Crose Law LLC; Bradley D. Crose

(57) ABSTRACT

A system and associated methods for animated image vision testing is disclosed. In at least one embodiment, a vision test includes at least one animated dynamic optotype image for measuring the visual acuity of a subject. The animated image vision test takes advantage of the ability of the human eyes to detect both distance and motion. Moving images, such as rotating segmented circles, let the eyes detect motion as to the size, distance, and rotation direction of that moving image. That motion detection is much more precise than the interpretation of multiple static letters or static images. Using rotating images for vision testing rather than static images creates an acuity test more accurate than current tests, a test that is faster to use, and a test that does not require the ability to read.

1 Claim, 17 Drawing Sheets

ANIMATED IMAGE VISION TEST

CROSS-REFERENCE TO RELATED APPLICATIONS

The present CIP patent application claims the benefit of priority of U.S. patent application Ser. No. 12/583,225 which is entitled "Animated Image Vision Test" filed on Aug. 17, 2009, and which is incorporated in full by reference herein.

TECHNICAL FIELD

The technology described herein relates generally to the field of vision testing devices and methods. More specifically, this technology relates to a device, system, and associated method for more accurately testing vision and acuity related to the correctness of prescriptions for eyeglasses and contact lenses.

BACKGROUND ART

The primary function of eyeglasses and contact lenses is in having the optical power of those lenses compensate for the loss of acuity (myopia) or excessive acuity (hyperopia) of the patient. Traditional vision acuity tests have used static optotypes as displays of printed or projected characters, objects, or shapes. Numerous patterns, configurations, and methods for static optotypes have been proposed for testing acuity based upon the ability of a subject to distinguish these various shapes, sizes, contrasts, and colors in tests such as Snellen charts, tumbling "E" arrays (static images of the letter "E" where the static image is also rotated 90 degrees, 180 degrees, and 270 degrees for discernment), Landolt "C" charts, and so on. Certain prior art vision testing patterns use periodic images, such as disks, rectangles, diamonds, etc.; others are quasi-periodic, such as tri-bar, and small checkerboard designs.

While the Landolt "C" chart is the clinical standard for acuity, the familiar Snellen eye testing chart as developed in 1862 using large, black, serifed letters on a white background is the test frequently used for determining visual acuity. The concept of these charts to verify acuity is based upon the patient seeing patterns such as letters or printed images on those charts, or as an image made visible by the reflection or projection of scattered light. Snellen's standard is that a person should be able to see and identify a 3.5 inch letter at a 20 foot distance (that ratio being 5 arc minutes in size and consistent regardless of its use in the "English" or Metric system). This, however, assumes that the ambient light is sufficiently bright so that the patient is able to identify the image and that there is sufficient contrast between the image and the background. A disadvantage of the Snellen type static images is that even defocused letters can still be partially recognized by their blur patterns. Much time is thus wasted as the patient, whose eyes are being tested, attempts to guess the letter. The design of the Snellen chart is further complicated by each letter having a different degree of recognizability and by the tendency of the patient to strain to perceive coherency when trying to identify the letters. Additionally, the precision of the Snellen test is incumbent upon the individual identifying three of the five letters displayed at a 20 foot distance. Identification of less than three letters indicates insufficient refraction; however identification of more than three letters is actually over-refraction. These factors create a potential for both over-refraction and over-compensation. Numerous other studies have shown difficulties with generating appropriate projected Snellen images as based upon technology developed in 1922 and updated in 1948. Projection systems are typically dependent upon a darkened room to enhance the contrast of the Snellen images, thereby creating a "contrast sensitivity" which may compromise actual acuity. Projection systems also inherently create a "fuzzy" image resulting from the mechanics of the diffraction of light waves, thus decreasing the accuracy and precision of the perceived refraction.

Numerous attempts have been made to utilize recent technology to reproduce the Snellen test concept on computers or other devices with a high contrast display. Images from electronically generated characters, such as those from a cathode ray tube (CRT) or liquid crystal display (LCD), produce images that are distinctly sharper and less confusing than print or projected images. Such displays eliminate the inherent fuzziness of the Snellen test, but they still do not eliminate the tendency to misperceive letters and images inherent in focusing on significantly distant static images.

Related patents known in the background art include the following: U.S. Pat. No. 6,402,320, issued to Borchert on Jun. 11, 2002, discloses methods and apparatus for measuring visual acuity in preverbial children.

The foregoing patent information reflects the state of the art of which the inventor is aware and is tendered with a view toward discharging the inventor's acknowledged duty of candor in disclosing information that may be pertinent to the patentability of the technology described herein. It is respectfully stipulated, however, that the foregoing patent and other information do not teach or render obvious, singly or when considered in combination, the inventor's claimed invention.

DISCLOSURE OF THE INVENTION

In various exemplary embodiments, the technology described herein provides a device, system, and associated method for more accurately testing vision and acuity related to the correctness of prescriptions for eyeglasses and contact lenses.

In one exemplary embodiment, the technology described herein provides a vision test. The vision test includes at least one animated dynamic optotype image shape for measuring the visual acuity of a subject. The animated dynamic optotype image can be scaled in size in such a way as to compare directly to the distance and acuity scale of Snellen and Landolt "C" vision tests on a visual display. The animated dynamic optotype image can include a rotating image. A viewing distance and a refraction of the at least one animated dynamic optotype image display can be varied to test vision. The animated dynamic optotype image can be scaled in size in such a way as to compare directly to the distance and acuity scale of a Landolt "C" vision test and Snellen vision test on a visual display.

In another exemplary embodiment, the technology described herein provides a method for testing vision. The method includes providing at least one animated dynamic optotype image shape for measuring the visual acuity of a subject and measuring the visual acuity of the subject with reference to the at least one animated dynamic optotype image shape. The method also can include providing at least one animated dynamic optotype image shape for measuring the visual acuity of a subject, wherein the animated dynamic optotype image is scaled in size in such a way as to compare directly to the distance and acuity scale of Snellen and Landolt "C" vision tests on a visual display, scaling the at least one animated dynamic optotype image, and comparing, directly, the scaled at least one animated dynamic optotype image to the distance and acuity scale of a Snellen vision test on the visual display. The method further can include providing at least one animated dynamic optotype image shape for measuring the visual acuity of a subject, wherein the animated dynamic optotype image comprises a rotating image and rotating the at least one animated dynamic optotype image. The method also can include providing at least one animated dynamic optotype image shape for measuring the visual acuity of a subject, wherein a viewing distance and a refraction of the animated dynamic optotype image display is varied to test vision and varying the viewing distance and the refraction of the animated dynamic optotype image display. The method further can include providing at least one animated dynamic optotype image shape for measuring the visual acuity of a subject, wherein the animated dynamic optotype image is scaled in size in such a way as to compare directly to the distance and acuity scale of a Landolt "C" vision test and Snellen vision test on a visual display and scaling the animated dynamic optotype in such a way as to compare directly to the distance and acuity scale of a Landolt "C" vision test and Snellen vision test on the visual display.

In yet another exemplary embodiment, the technology described herein provides a vision test system for more accurately testing vision and acuity related to the correctness of prescriptions for eyeglasses and contact lenses. The vision test system includes a plurality of interchangeable animated dynamic optotype image shapes, each shape adapted for use to measure the visual acuity of a subject, wherein each of the plurality of interchangeable animated dynamic optotype images comprises a rotating image. Each of the plurality of interchangeable animated dynamic optotype images can be scaled in size in such a way as to compare directly to the distance and acuity scale of Snellen and Landolt "C" vision tests on a visual display. A viewing distance and a refraction of the each of the plurality of interchangeable animated dynamic optotype images can be varied to test vision. Each of the plurality of interchangeable animated dynamic optotype images can be scaled in size in such a way as to compare directly to the distance and acuity scale of a Landolt "C" vision test and Snellen vision test on a visual display.

In yet another exemplary embodiment, the technology described herein provides A visual acuity test comprising:
a display surface;
at least one animated non-static rotating dynamic optotype image shape displayed upon the display surface, the at least one non-static rotating dynamic optotype image shape having an image size_that remains fixed during the visual acuity test, a plurality of non-contiguous image segments with image gaps between the non-contiguous image segments, the image segments having a segment size that remains fixed during the visual acuity test and a segment color, the image gaps having a uniform gap separation distance;
a viewing distance between the at least one animated non-static rotating dynamic optotype image shape and a subject being tested for visual acuity;
a rate of rotation of the at least one animated non-static rotating dynamic optotype image shape;
a direction of rotation;
a dynamic optotype viewing direction;
a background color, the background color contrasting with the segment color; and a visual acuity threshold determination obtained_by varying at least one of the rate of rotation, the image size, the image segment size, the image gaps, the image segment color, the background color, and the direction of rotation a left fixation point; a right fixation point;
a fixation point separation;
a left fixation point viewing direction; and a right fixation point viewing direction;
wherein the viewing distance is substantially equal to the viewing distance of a Snellen or Landolt vision test.

Advantageously, the technology described herein provides an improved method for more accurately and more rapidly perceiving visual acuity. Also advantageously, the technology described herein provides an improved vision test chart.

There has thus been outlined, rather broadly, the more important features of the technology in order that the detailed description thereof that follows may be better understood, and in order that the present contribution to the art may be better appreciated. There are additional features of the technology that will be described hereinafter and which will form the subject matter of the claims appended hereto. In this respect, before explaining at least one embodiment of the technology in detail, it is to be understood that the invention is not limited in its application to the details of construction and to the arrangements of the components set forth in the following description or illustrated in the drawings. The technology described herein is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the technology described herein. It is important, therefore, that the claims be regarded as including such equivalent constructions insofar as they do not depart from the spirit and scope of the technology described herein.

Further objects and advantages of the technology described herein will be apparent from the following detailed description of a presently preferred embodiment which is illustrated schematically in the accompanying drawings.

BRIEF DESCRIPTION OF DRAWINGS

The technology described herein is illustrated with reference to the various drawings, in which like reference numbers denote like device components and/or method steps, respectively, and in which.

BEST MODE FOR CARRYING OUT THE INVENTION

Figure 1:
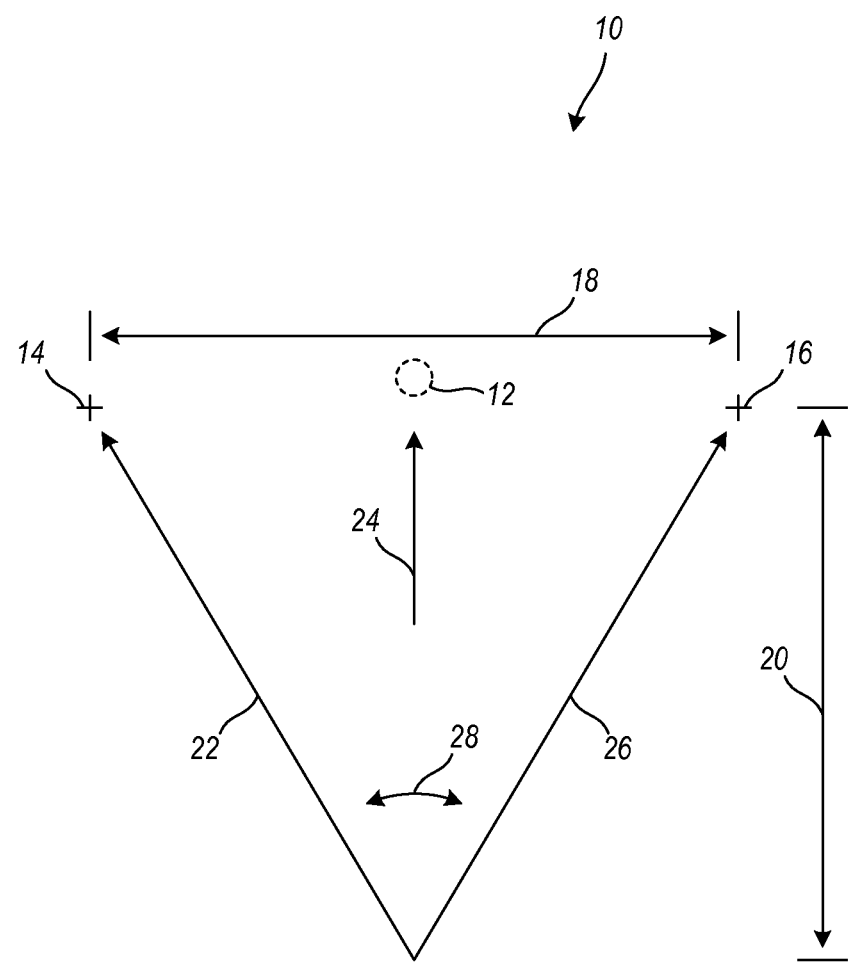
FIG. 1 is a schematic diagram of a dynamic optotype computer image benchmark configuration, according to an embodiment of the technology described herein.

Before describing the disclosed embodiments of this technology in detail, it is to be understood that the technology is not limited in its application to the details of the particular arrangement shown here since the technology described is capable of other embodiments. Also, the terminology used herein is for the purpose of description and not of limitation.

In various exemplary embodiments, the technology described herein provides a device, system, and associated method for more accurately testing vision and acuity related to the correctness of prescriptions for eyeglasses and contact lenses.

A dynamic optotype is a rotating geometric figure, such as a segmented circle, a triangle, or other shape having dimensions and a rotation rate such that its motion can just be perceived at a specified viewing distance by a subject whose vision is or has been corrected to the accepted 20/20 standard. Unlike static optotype tests, the dynamic optotype acuity test utilizes the physiology and sensitivity of the photoreceptors in the eye to determine a precise acuity threshold instead of the subjective cognition of static images viewed at a fixed distance. The dynamic optotype concept is essentially the inverse of pixels being viewed on an electronic display whereby viewing those pixels at a sufficient distance causes the pixels to merge into an apparent image. The dynamic optotype motion lets the eye's photoreceptors function much as "screen pixels" where the detection of motion of the dynamic optotype creates an acuity threshold (the distance beyond which motion, either clockwise or counter-clockwise, is not perceivable) at a fixed arc degree width related to the diameter of the dynamic optotype, the gap width and gap height of the dynamic optotype, the color and shading and intensity of the dynamic optotype versus the background contrast, and the distance of the observer from that dynamic optotype.

In using the innate physiology of the photoreceptors, the dynamic optotype acuity threshold has numerous advantages over the subjective 60% accuracy and interpretation rate of the Snellen and other static optotype tests. Ironically, correctly identifying all of the letters of the Snellen test may result in a prescription too strong for mid-range reading or computer use. The increased precision of the dynamic optotype acuity test is not dependent upon the subjects' ability to read (regardless of the subjects' language or reading skills). The increased precision of the dynamic optotype test also tends to reduce the time spent attempting to interpret and comprehend the letters and shapes used in static optotype acuity tests, thus decreasing the time necessary to determine the correct acuity diagnosis.

The technology described herein provides creates a dynamic optotype that permits an accurate determination of acuity and allows patients to more accurately perceive visual acuity than they can by use of static reflected or projected letters, symbols, or shapes as used by the Snellen and similar tests. A dynamic optotype is a rotating geometric figure, such as a segmented circle, a triangle, or other shape having dimensions and a rotation rate such that its motion can just be perceived at a specified viewing distance by a subject whose vision is or has been corrected to the accepted 20/20 standard. Dynamic optotypes allow the patient to more accurately discern whether test images are either insufficiently or excessively magnified by the prescription optics thereby substantially improving the aforementioned prior art by providing a superior vision test chart and a method for rapidly and reliably testing a patient's ability to perceive image contrasts as a function of image size.

The novel test method uses animated dynamic optotype images (for example, one or more rotating segmented circles and shapes and colored dots of varying size, contrast, and color) on any type of visual display or projected image with the advantage of the dynamic optotype images creating an acuity threshold (at the refraction and distance from the dynamic optotype beyond which motion, either clockwise or counter-clockwise, is not perceivable.) Dynamic optotypes also have an increased sharpness not available with the blurriness associated with projected or reflected static images. Unlike the Snellen or other static optotype tests, the patient does not rely on (the 60% accuracy of) guessing the identity of the letters(s) and shapes, but rather is able, based upon the appropriate refraction and distance from the animated image, to determine a precise acuity threshold for that dynamic optotype image.

That acuity threshold (perception of motion of a specific size image from a specific distance) correlates to the specific visual acuity. In looking at animated dynamic optotype images, the patient either sees the motion of the particularly sized dynamic optotype image because the viewing distance is close enough and the acuity refraction is sufficient, or the patient does not see the motion because the because the distance is too far and the acuity refraction is insufficient. This gives a much more accurate acuity threshold than is possible with the Snellen Test. Unlike the Snellen test, the subject does not need to be able to read English letters to identify the acuity threshold, and if the subject is able to identify the direction of motion of the dynamic optotypes, the subject does not even need to be able to read.

The variations in size of the dynamic optotype images correspond to similar sized letters associated with the static images of the Snellen test, or static shapes of the Task test or the Landolt "C" test. The animated nature of the image shape (s) allows the patient to also avoid the subjective interpretive cognition of letters or symbols typical of the static Snellen type characters. The patient's perception of the acuity threshold of the motion of the animated dynamic optotype images, however, can be directly correlated to the refraction distance of the Snellen test.

Figure 2:
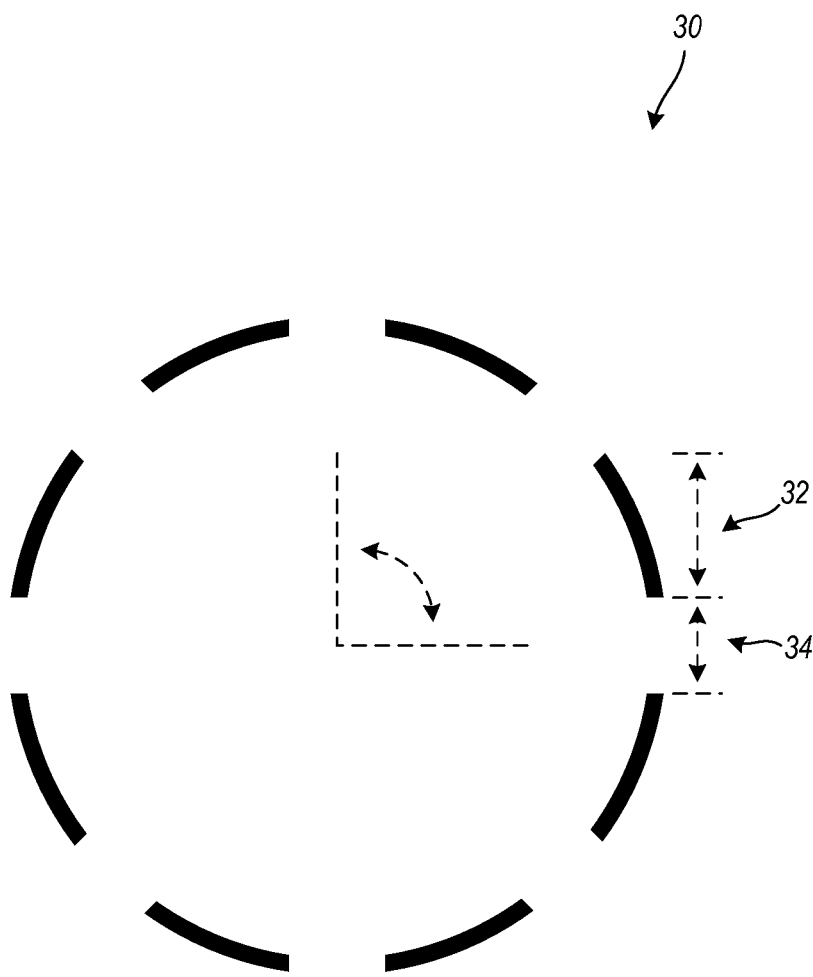
FIG. 2 is a schematic diagram of the dynamic optotype gap and segment height in circumferential degrees for a circular dynamic optotype, wherein the sum of the circumferential degrees of the segment heights and gap heights will be 360 degrees, according to an embodiment of the technology described herein.

The test is primarily designed to be viewed on a standard computer monitor or projected image at distances equivalent to and corresponding to the Snellen Test. Typical dynamic optotype image dimensions (i.e. the diameter of rotating dynamic optotype segmented circles) that correspondence to the standard Snellen measurements are in Table 1. An 88 mm (~3.5 inch) high Snellen letter viewed at 6 meters (~20 feet) would typically have an acuity threshold equivalent to a rotating dynamic optotype segmented circle with a displayed screen diameter of 16 mm. The precise acuity threshold of a specific dynamic optotype as a ratio between the dynamic optotype diameter and the viewing distance (regardless of it measurement system) is determined by the shape, angular motion, rotation speed, gap width, gap height, color, background contrast, and image intensity. For example, in one preferred embodiment of the invention, a segmented circular dynamic optotype such as is shown in FIG. 2 can be employed.

TABLE 1

Typical Dynamic Optotype Equivalents to Snellen Test Letter Heights

| Snellen distance Feet | Snellen distance Meters | Snellen Letter Image Height Inches | Snellen Letter Image Height Millimeters | Typical Dynamic Optotype Image Diameter Millimeters |
|---|---|---|---|---|
| 60 | 24 | 14 | 352 | 42 |
| 30 | 12 | 7.0 | 176 | 21 |
| 20 | 6 | 3.5 | 88 | 14 |
| 10 | 3 | 1.75 | 44 | 7 |
| 5 | 1.5 | 0.87 | 22 | 3.5 |

Referring now to FIG. 1, a dynamic optotype computer image benchmark configuration 10 is shown. The configuration 10 includes a typical dynamic optotype image 12. The configuration 10 includes a left fiducial (calibration) point 14 and a right fixation point 16. The configuration 10 includes a benchmark fiducial (calibration) point separation 18. By way of example the benchmark fiducial (calibration) point separation 18 is 20.0 cm such that when viewed at a distance of 57 cm the fiducial (calibration) points have a separation of 20 arc degrees. The configuration 10 includes viewing distance 20. The configuration 10 includes a viewing direction 22 towards the left fiducial (calibration) point 14. The configuration 10 includes a viewing direction 24 towards the dynamic optotype 12. The configuration 10 includes a viewing direction 26 towards the right fiducial (calibration) point 16. The configuration 10 includes a separation width 28 between the fiducial (calibration) points 14, 16. By way of example, the separation width 28 is a 20 arc degree separation width of fiducial (calibration) points 14, 16 when they are at a separation distance of 20.0 cm apart and viewed at a distance of 57 cm.

Referring now to FIG. 2, a schematic diagram 30 of the dynamic optotype gap height 34 and segment height 32 in circumferential degrees for a circular dynamic optotype is shown. The sum of the circumferential degrees of the segment heights and gap heights is 360 degrees.

Figure 3:
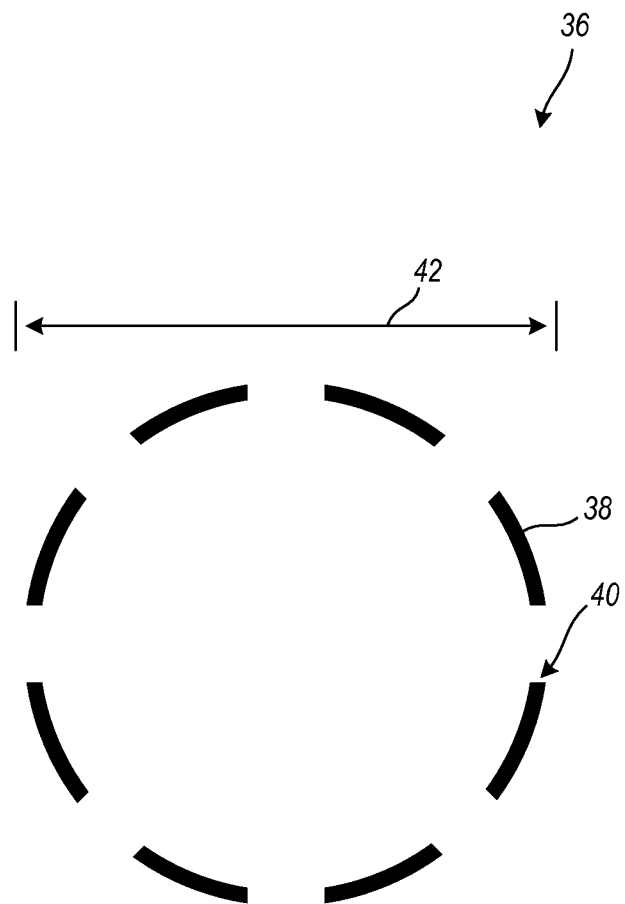
FIG. 3 is a schematic diagram of a typical segmented circular dynamic optotype, illustrating, in particular, a gap (and segment) width (thickness) of approximately 4% as a percent of the dynamic optotype diameter, according to an embodiment of the technology described herein.

Referring now to FIG. 3, a schematic diagram 36 of a typical segmented circular dynamic optotype is shown. The typical segmented circular dynamic optotype 36 includes dynamic optotype segment 38, a gap (and segment) width (thickness) 40 of approximately 4% as a percent of the dynamic optotype diameter 42.

Figure 4:
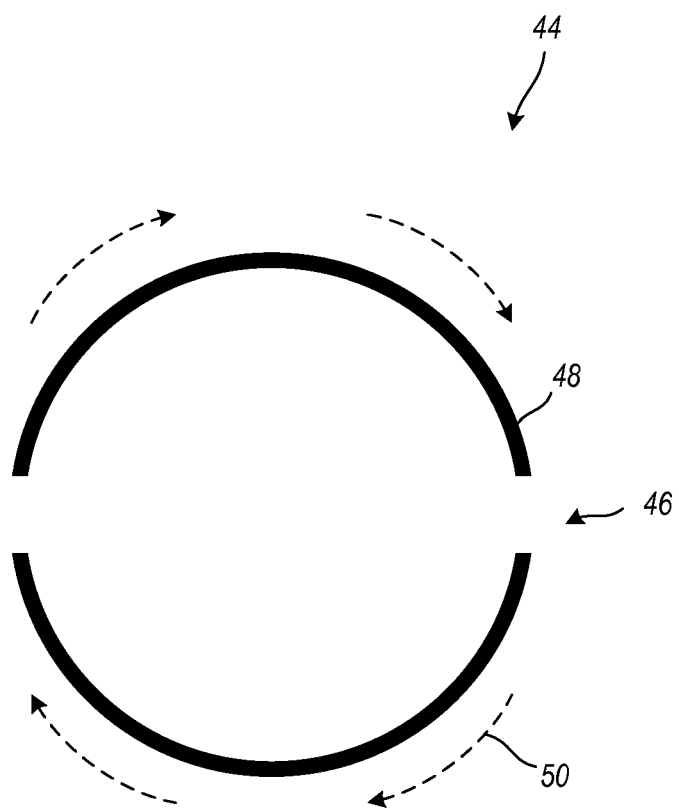
FIG. 4 is a schematic diagram of a static image of a 2 segment animated dynamic optotype image rotating clockwise, according to an embodiment of the technology described herein.

Referring now to FIG. 4 a static image of a 2 segment animated dynamic optotype image 44 is shown, rotating clockwise 50. The 2 segment animated dynamic optotype image 44 includes image segment 48 and image gap height 46.

Figure 5:
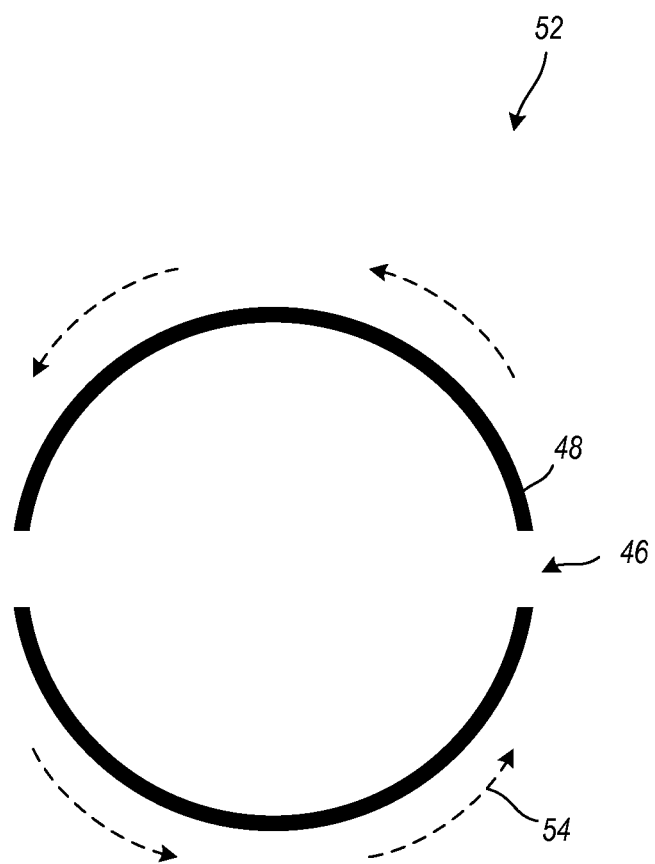
FIG. 5 is a schematic diagram of a static image of a 2 segment animated dynamic optotype image rotating counter clockwise, according to an embodiment of the technology described herein.

Referring now to FIG. 5 a static image of a 2 segment animated dynamic optotype image 52 is shown, rotating counter clockwise 54. The 2 segment animated dynamic optotype image 52 includes image segment 48 and image gap height 46.

Figure 6:
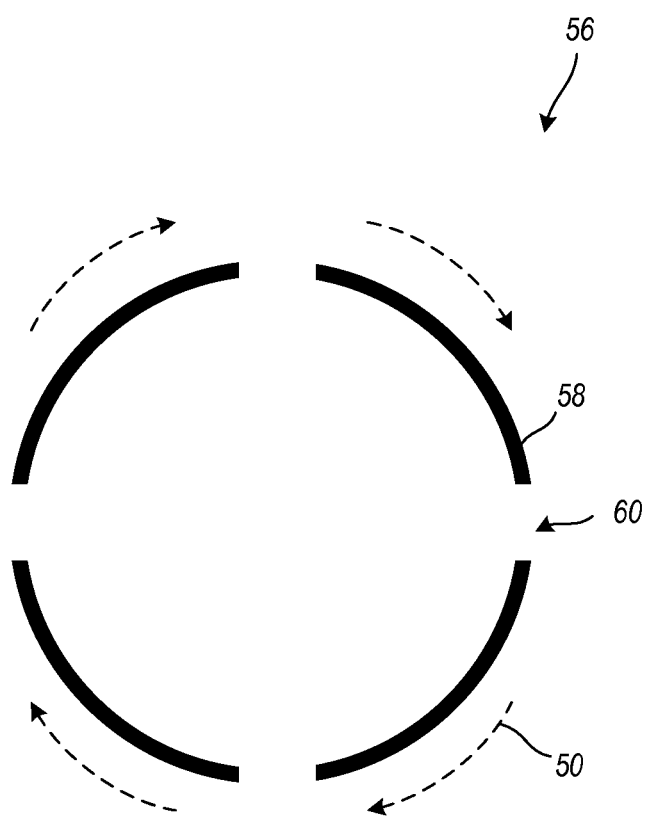
FIG. 6 is a schematic diagram of a static image of a 4 segment animated dynamic optotype image rotating clockwise, according to an embodiment of the technology described herein.

Referring now to FIG. 6, a static image of a 4 segment animated dynamic optotype image 56 is shown, rotating clockwise 50. The 4 segment animated dynamic optotype image 56 includes image segment 58 and image gap height 60.

Figure 7:
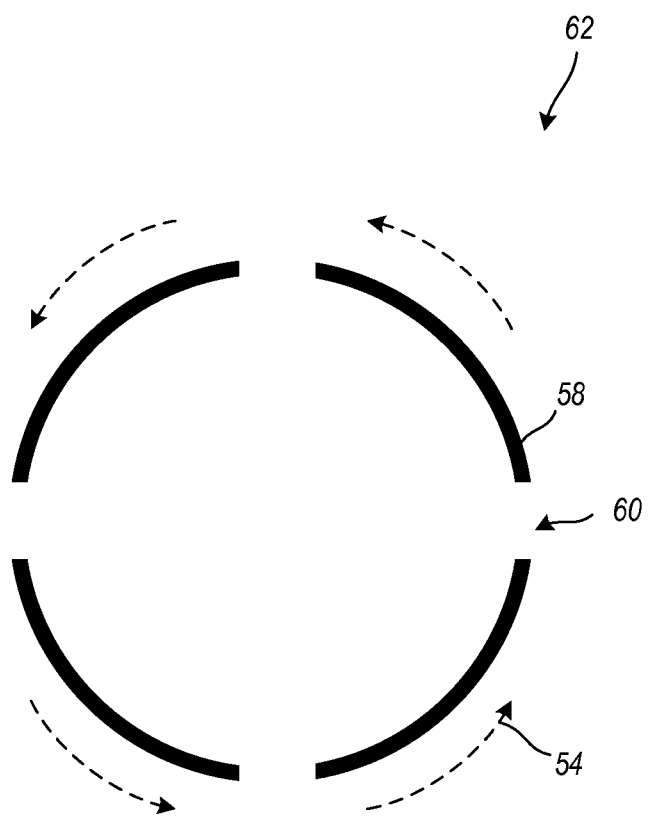
FIG. 7 is a schematic diagram of a static image of a 4 segment animated dynamic optotype image rotating counter clockwise, according to an embodiment of the technology described herein.

Referring now to FIG. 7, a static image of a 4 segment animated dynamic optotype image 62 is shown, rotating counter clockwise 54. The 4 segment animated dynamic optotype image 62 includes image segment 58 and image gap height 60.

Figure 8:
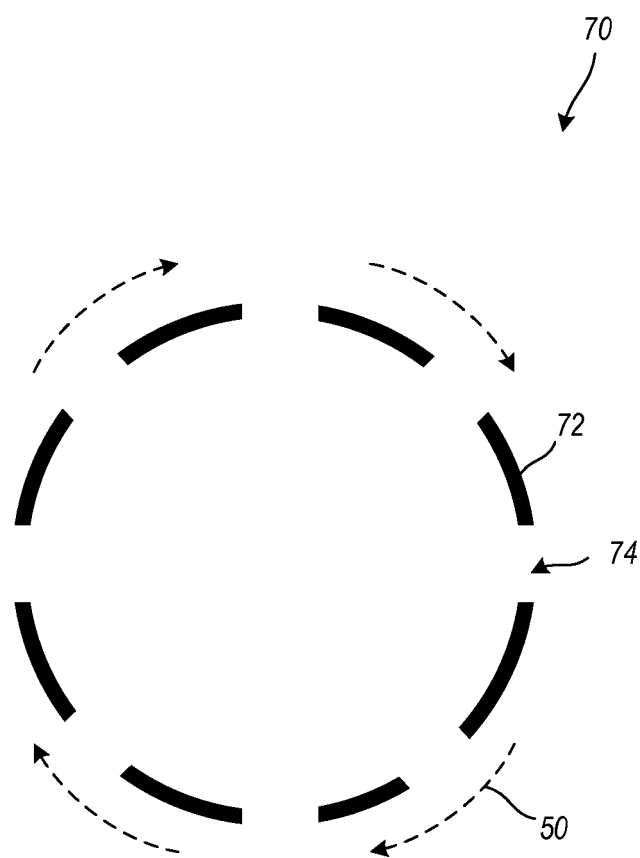
FIG. 8 is a schematic diagram of a static image of a 8 segment animated dynamic optotype image rotating clockwise, according to an embodiment of the technology described herein.

Referring now to FIG. 8, an 8 segment animated dynamic optotype image 70 is shown, rotating clockwise 50. The 8 segment animated dynamic optotype image 70 includes image segment 72 and image gap height 74.

Figure 9:
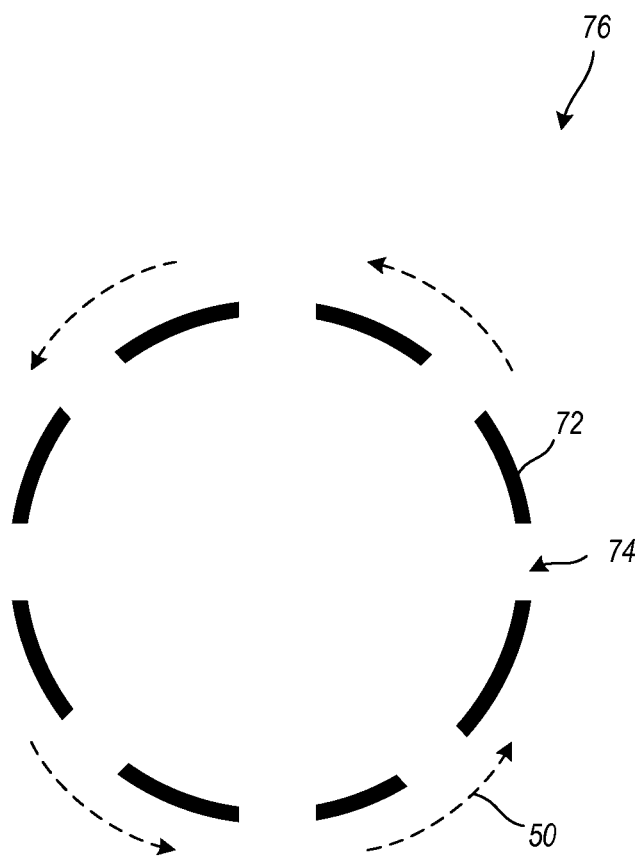
FIG. 9 is a schematic diagram of a static image of a 8 segment animated dynamic optotype image rotating counter clockwise, according to an embodiment of the technology described herein.

Referring now to FIG. 9, an 8 segment animated dynamic optotype image 76 is shown, rotating counter clockwise 54. The 8 segment animated dynamic optotype image 76 includes image segment 72 and image gap height 74.

Figure 10:
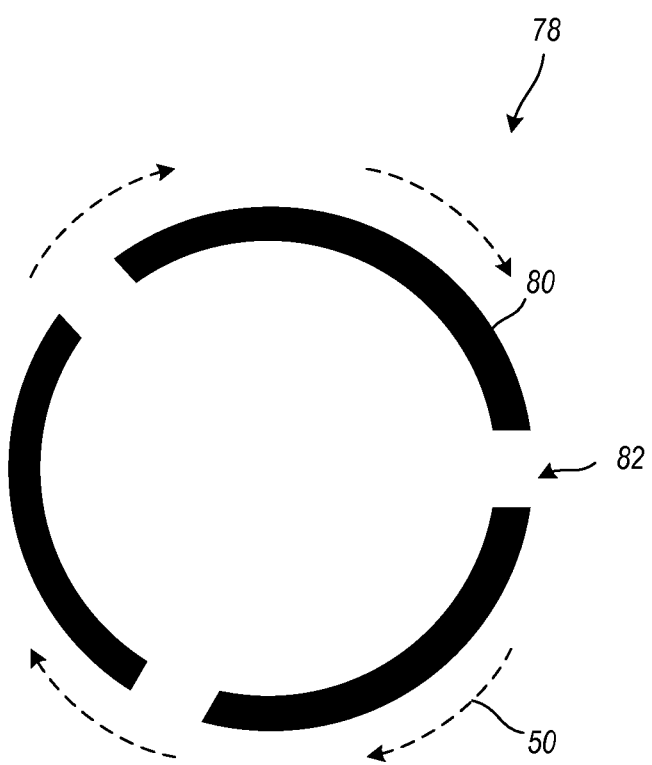
FIG. 10 is a schematic diagram of a static image of a 3 segment animated dynamic optotype image rotating clockwise with a larger gap and segment width/thickness (approximately 10%), according to an embodiment of the technology described herein.

Referring now to FIG. 10, a 3 segment animated dynamic optotype image 78 is shown, rotating clockwise 50. The 3 segment animated dynamic optotype image 78 includes image segment 80 and image gap height 82.

Figure 11:
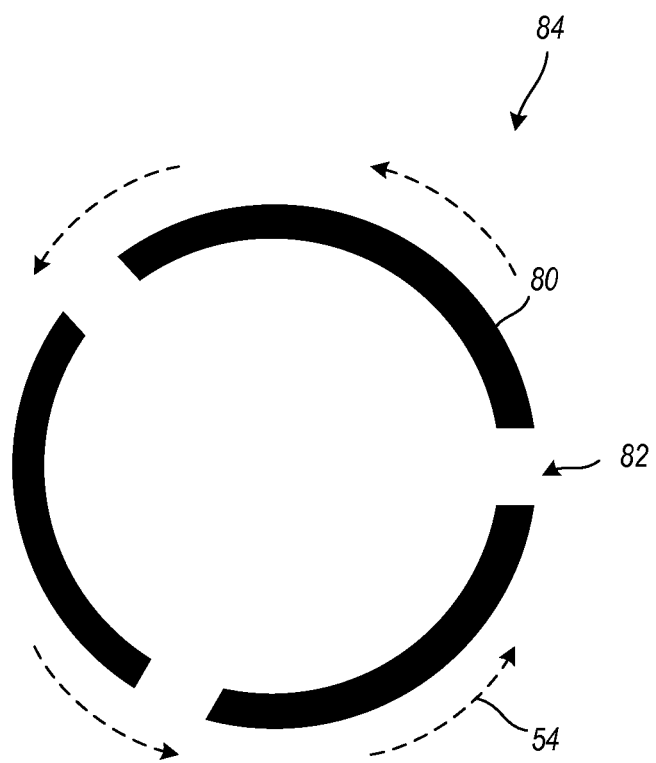
FIG. 11 is a schematic diagram of a static image of a 3 segment animated dynamic optotype image rotating counter clockwise with a larger gap and segment width/thickness (approximately 15%), according to an embodiment of the technology described herein.

Referring now to FIG. 11, a 3 segment animated dynamic optotype image 84 is shown, rotating counter clockwise 54. The 3 segment animated dynamic optotype image 84 includes image segment 80 and image gap height 82. The 3 segment animated dynamic optotype image 84 includes a larger gap and segment width/thickness (approximately 15%).

Figure 12:
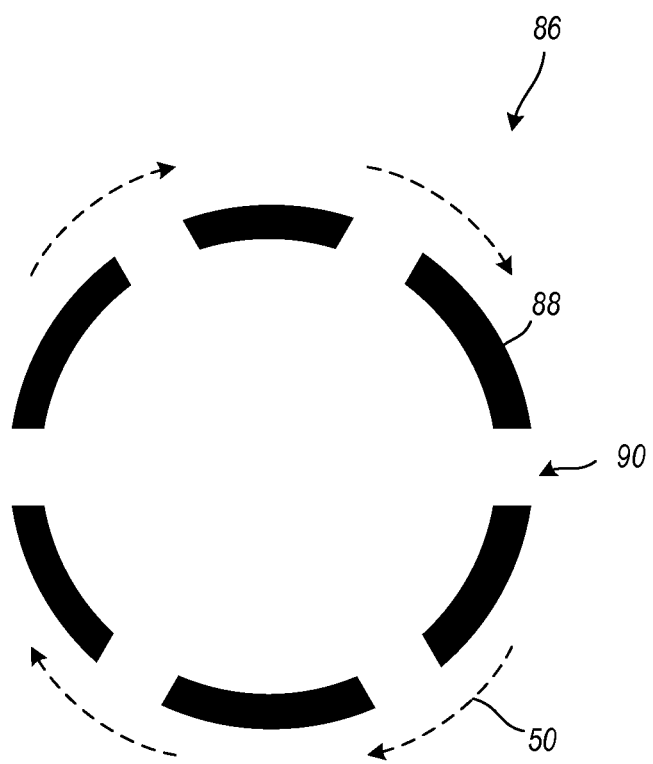
FIG. 12 is a schematic diagram of a static image of a 6 segment animated dynamic optotype image rotating clockwise with a larger gap and segment width/thickness (approximately 10%), according to an embodiment of the technology described herein.

Referring now to FIG. 12, a 6 segment animated dynamic optotype image 86 is shown, rotating clockwise 50. The 6 segment animated dynamic optotype image 86 includes image segment 88 and image gap height 90. The 6 segment animated dynamic optotype image 86 includes a larger gap and segment width/thickness (approximately 10%).

Figure 13:
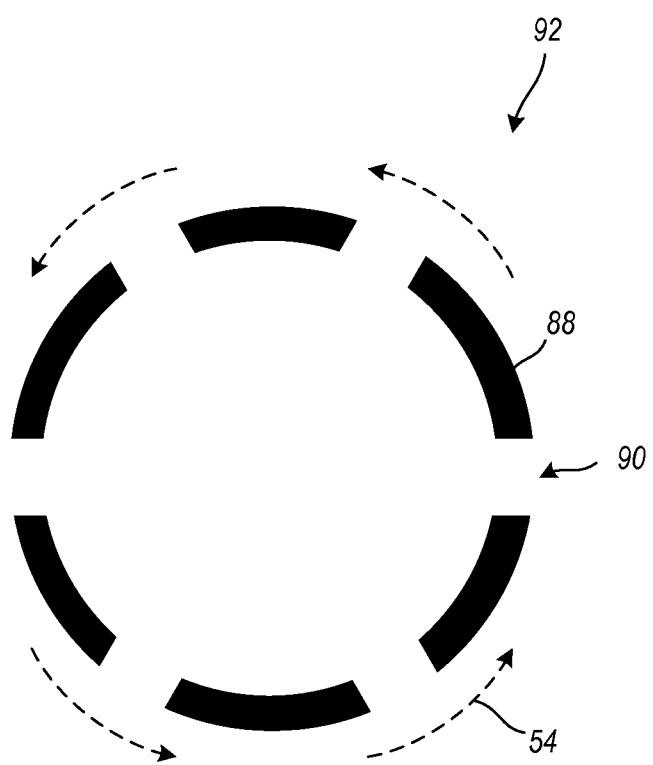
FIG. 13 is a schematic diagram of a static image of a 6 segment animated dynamic optotype image rotating counter clockwise with a larger gap and segment width/thickness (approximately 20%), according to an embodiment of the technology described herein.

Referring now to FIG. 13, a 6 segment animated dynamic optotype image 92 is shown, rotating counter clockwise 54. The 6 segment animated dynamic optotype image 92 includes image segment 88 and image gap height 90. The 6 segment animated dynamic optotype image 92 includes a larger gap and segment width/thickness (approximately 20%).

Figure 14:
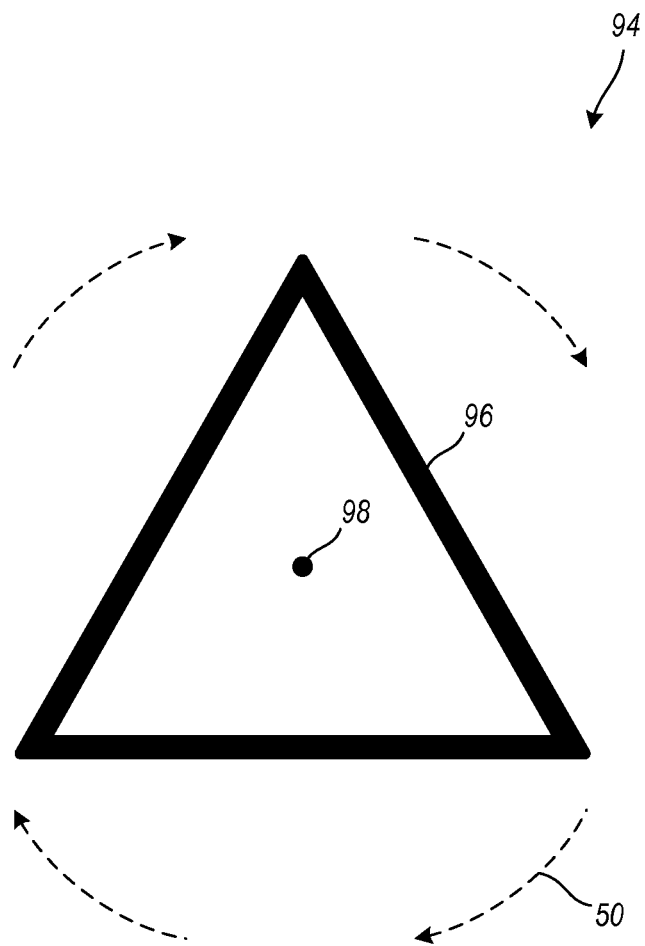
FIG. 14 is a schematic diagram of a static image of a triangular animated dynamic optotype image rotating clockwise, according to an embodiment of the technology described herein.

Referring now to FIG. 14, a triangular animated dynamic optotype image 94 is shown, rotating clockwise, 50. The triangular animated dynamic optotype image 94 includes image segment 96 rotating about a center point of rotation 98.

Figure 15:
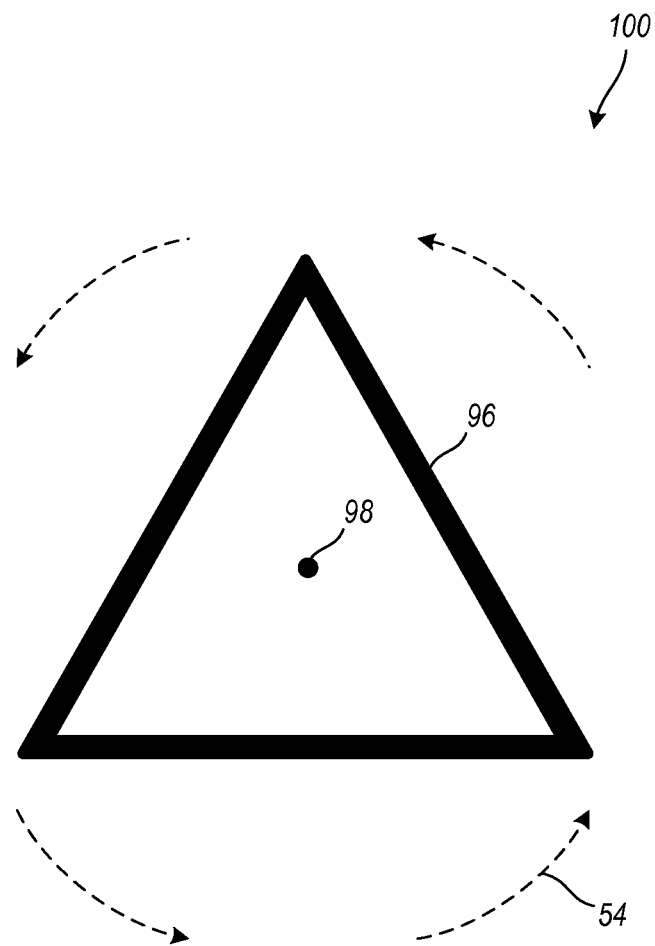
FIG. 15 is a schematic diagram of a static image of a triangular animated dynamic optotype image rotating counter clockwise, according to an embodiment of the technology described herein.

Referring now to FIG. 15, a triangular animated dynamic optotype image 100 is shown, rotating counter clockwise, 54. The triangular animated dynamic optotype image 94 includes image segment 96 rotating about a center point of rotation 98.

Figure 16:
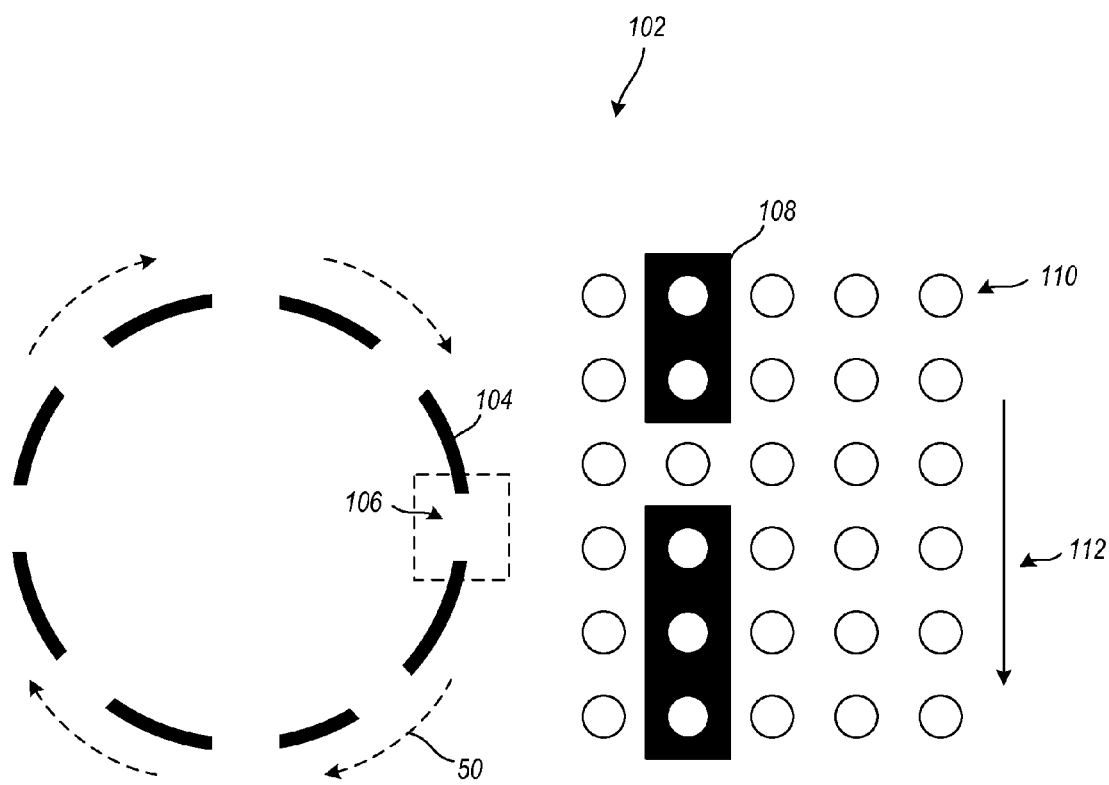
FIG. 16 is a schematic diagram illustrating the representation path of a thin segmented circular dynamic optotype image crossing the photoreceptors of the eye, according to an embodiment of the technology described herein.

Referring now to FIG. 16, a schematic diagram 102 is shown, illustrating the representation path of a thin segmented circular dynamic optotype image crossing the photoreceptors of the eye. The thin segmented circular dynamic optotype image includes image segment 104 and thin gap (and segment) dynamic optotype image 106, rotating clockwise 50. The diagram 102 illustrates representation of photoreceptor distribution 110, representation path of image gap across the photoreceptors 108, and direction of motion of the dynamic optotype image gap 112.

Figure 17:
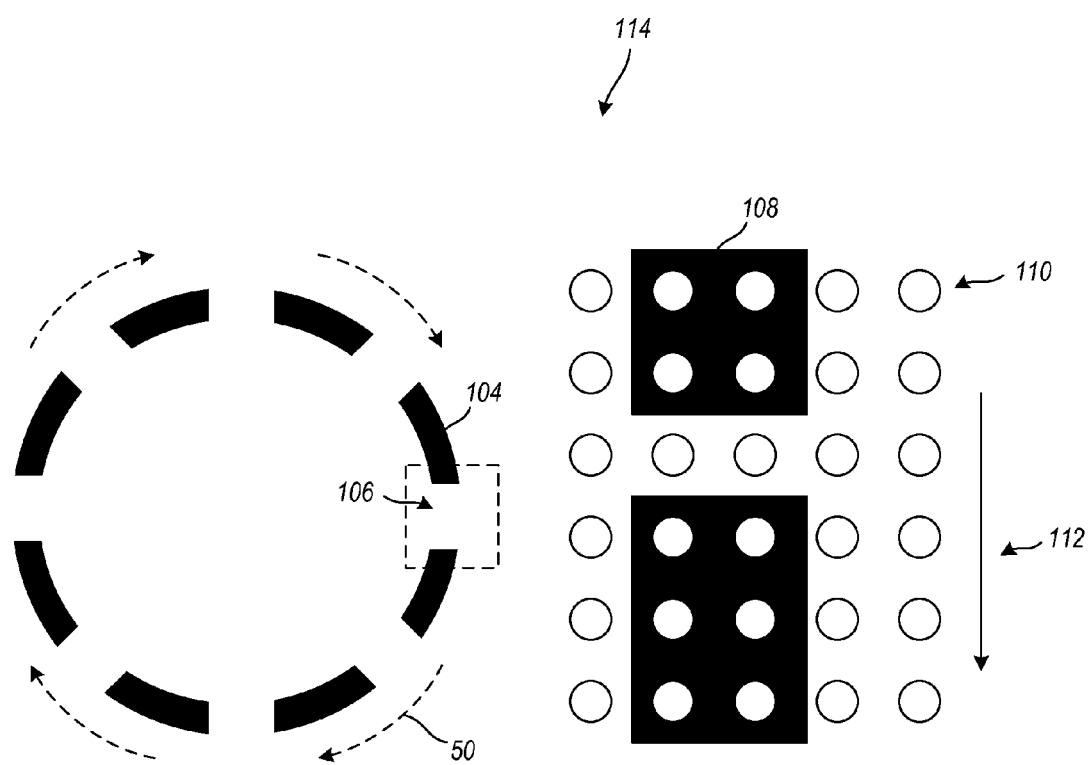
FIG. 17 is a schematic diagram of illustrating the representation of path of a thick segmented circular dynamic optotype image crossing the photoreceptors of the eye, according to an embodiment of the technology described herein.

Referring now to FIG. 17, a schematic diagram 114 is shown, illustrating the representation of path of a thick segmented circular dynamic optotype image crossing the photoreceptors of the eye. The thin segmented circular dynamic optotype image includes image segment 104 and thin gap (and segment) dynamic optotype image 106, rotating clockwise 50. The diagram 114 illustrates representation of photoreceptor distribution 110, representation path of image gap across the photoreceptors 108, and direction of motion of the dynamic optotype image gap 112.

An animated dynamic optotype is a rotating segmented image which provides a precise measure of visual acuity whereby the angular arc width of the image and the viewing distance from the image are directly proportional to an individual's visual acuity Because of the innate preference of the eye to detect moving images more precisely than static images, the animated dynamic optotype provides a more precise and faster method of visual acuity determination. Current visual testing uses static images as optotypes are not as precise and are significantly dependent upon cognition for determination rather than on the physiological response of the eye.

The animated dynamic optotype image rotates around a central axis and can thereby be calibrated as to angular arc width, segment number, segment width, rotation rate, and background contrast. The image is reduced in angular size until the subject can no longer detect the image rotation whereby the calibrated angular width of the smallest image where rotation can be detected is the indicator of visual acuity for the purposes of determining refraction.

A segmented shape such as a circle consisting of one or more gaps and segments is rotated around a central axis and the calibrated angular width of the shape is adjusted such that a subject with 20/20 vision is able to detect the rotation of the shape at a distance directly proportional to the angular width. The refraction need for a subject to have 20/20 vision is directly proportional to the difference between the actual perceived angular width arc diameter of the shape and the angular width of the shape to achieve ideal 20/20 visual acuity.

The functionality of the animated dynamic optotype lets it be used in several unique additional applications such as the following:

Drop™ Infant Acuity Test

Because of the ability of the eye to detect motion, that motion detection is preferential in getting the attention of subjects even at an early age or infancy. Infants and children and non-verbal individuals will preferentially look at and towards a moving and rotating object rather than look at a static image.

Using a rotating animated optotype image on one side of a display such as a computer monitor versus a similar static image on the other side of the display will have the infant and child preferentially look at the rotating image rather than the static image. The images may have black and white segments and gaps on a contrasting background that may range from white background, through a gray background, to a black background. When the locations of the rotating and static images are reversed, the attention, and focus (as evidenced by eye and head motion) of the infant and child will move to follow the location of the rotating image. Sequentially reducing the angular arc width size of the image will have the following of the rotating image continue regardless of the side location of the rotating image until the angular arc width size of that image is insufficient and too small to produce a visual acuity response. The inability to differentiate between the moving and static image will provoke a rapid search and associated eye and head movements between the two images as the infant and child tries to determine which image and set of image is rotating versus which image and set of images is static. The angular arc width size of the image point at which the infant and child can still determine the rotation serves as a measure of the infant and child's visual acuity.

Item 1—Test images may rotating or static.

Item 2—Test images may be static or rotating.

Item 3—Image size indicator

Drop™ Infant Color Acuity Test

A test similar to the Drop™ Infant Acuity test uses colored images such as having segments that are red, segments that are green, segments that are blue, and segments of other primary colors and with backgrounds that are contrasting and may range from black to gray to white and of varying other colors.

Using a matching colored rotating animated optotype image on one side of a display such as a computer monitor versus a similar static image on the other side of the display will have the infant and child preferentially look at the rotating image rather than the static image. The images may have segments that are red, segments that are green, segments that are blue, and segments of other primary colors and with backgrounds that are contrasting and may range from black to gray to white and of varying other colors. When the locations of the rotating and static images are reversed, the attention, and focus (as evidenced by eye and head motion) of the infant and child will move to follow the location of the rotating image. Sequentially reducing the angular arc width size of the image will have the following of the rotating image continue regardless of the side location of the rotating image until the angular arc width size of that image is insufficient and too small to produce a visual acuity response. The inability to differentiate between the moving and static image will provoke a rapid search and associated eye and head movements between the two images as the infant and child tries to determine which image and set of image is rotating versus which image and set of images is static. The angular arc width size of the image point at which the infant and child can still determine the rotation serves as a measure of the infant and child's visual acuity and perception of that specific color.

Item 1—Test images may rotating or static and may be colored rather than black and white and backgrounds may be colored rather than gray.

Item 2—Test images may be static or rotating and may be colored rather than black and white and backgrounds may be colored rather than gray.

Item 3—Image size indicator

Acuity Test for Dyslexics

Dyslexia is perceived as a difficulty with the cognition of letters and numbers usually associated with the tendency to see those characters as a reversal of the character and number, or as a region of double images, or seeing the character and number as being disjointed from the adjacent characters and numbers. The images may have black and white segments and gaps on a contrasting background that may range from white background, through a gray background, to a black background. Because determination of visual acuity using rotation diction of the animated dynamic optotype is not dependent upon the static orientation of the image but rather the calibrated arc width of the image, a determination of acuity for someone with dyslexia using an animated dynamic optotype will be more precise and not have the orientation difficulties associated with someone who has dyslexia using a static image acuity test.

Item 1—Animated dynamic optotypes with varying calibrated arc width diameters.

Item 2—Image scale indicating the optotype arc width diameter in comparison to 20/20 acuity values.

Color Perception Test

Visual acuity for color perception may be measured by using animated dynamic optotype images with segments that may be red, segments that may be green, segments that may be blue, and segments of other primary colors and combinations and with backgrounds that are contrasting and may range from black to gray to white and of varying other colors. The varying arc width of the images allows the precise determination of acuity for those specific colors. Such a test may also be determinant as to whether there is a chromatic characteristic to acuity in that some colors may be more perceptible than other leading to difficulties in perception, reading, and other cognitive skills.

Item 1—Animated dynamic optotypes with varying calibrated arc width diameters which may be colored rather than black and white and backgrounds may be colored rather than gray.

Item 2—Image scale indicating the optotype arc width diameter in comparison to 20/20 acuity values.

Dyslexia Color Screening Test

Rows of animated dynamic optotypes with identical arc width diameters may be displayed and the subjects ability to detect and clearly see the specific optotypes as displayed in that visual row can be used as an indicator of the arc range of visual perception. The advantages of someone using a animated dynamic optotype to test for visual dyslexia using images that may have black and white segments and gaps on a contrasting background that may range from white background, through a gray background, to a black background applies to using images that may have segments that are red, segments that are green, segments that are blue, and segments of other primary colors and with backgrounds that are contrasting and may range from black to gray to white and of varying other colors. The varying arc width of the images allows the precise determination of acuity for those specific colors. Such a test may also be determinant as to whether there is a chromatic characteristic to acuity in that some colors may be more perceptible than other leading to difficulties in perception, reading, and other cognitive skills.

Item 1—Animated dynamic optotypes for comparison with identical arc width diameters and varying colors on backgrounds that may be white, gray, black, and colored.

Item 2—Image label indicating the optotype color.

Peripheral Range Test

A range of animated dynamic optotypes may be displayed and the subjects ability to detect and clearly see the specific optotypes as displayed in that visual range can be used as an indicator of the range of visual perception. This is especially appropriate for wearers of progressive lenses which have a limited horizontal range of clear vision due to the inherent astigmatic areas of the lenses.

Item 1—A row of animated dynamic optotypes for comparison with identical arc width diameters and varying colors on backgrounds that may be white, gray, and black.

Item 2—Focal point for starting the test where the head remains stationary while the eyes move across the visual range.

Item 3—Image labels indicating the range of undistorted optotype vision.

Item 4—Arrow indicating the direction of eye (only) movement to detect the visual range.

Item 5—Colored static images of varying colors to indicate chromatic shift due to the image distortion.

Peripheral Field Test

A field of animated dynamic optotypes may be displayed and the subjects ability to detect and clearly see the specific optotypes as displayed in that visual field can be used as an indicator of the field of visual perception.

Item 1—Rows and columns of calibrated animated dynamic optotypes

Item 2—Index numbers indicating the row and column

Visual Perception/Comprehension Indication Test

Some illnesses have a comprehension and cognition factor associated with them such as Alzheimer's disease, Amyotrophic lateral sclerosis (ALS) or Lou Gehrig's disease, or loss of mental function resulting from physical injuries. A combination of visual field perception tests and color perception tests using animated dynamic optotypes might facilitate the diagnosis of such comprehension and cognition as well a quantify the status of such conditions, Item 1—Rows and columns of calibrated animated dynamic optotypes with sizes and colors of the calibrated animated dynamic optotypes that will vary to indicate differences in perception.

Item 2—Index numbers indicating the row and column

Distance Perception System

An animated dynamic optotype of a specific arc width diameter may be displayed such that a subject with 20/20 visual acuity is able to detect the rotating motion of that image only when they are sufficiently within the threshold of that image detection. The ability of detect that motion for someone with 20/20 visual acuity serves as a measure of the distance of the viewer to that animated dynamic optotype.

Item 1—An animated dynamic optotype of a specific arc width diameter whose rotation will be visible to the subject with 20/20 visual acuity at less than a specific distance.

Item 2—The arc width range of visibility of the animated dynamic optotype.

Item 3—Viewing subject

Distance Warning System

An animated dynamic optotype of a specific arc width diameter may be displayed such that a subject with 20/20 visual acuity is able to detect the rotating motion of that image only when they are sufficiently within the threshold of that image detection. An example of such an application might be a rotating red animated dynamic optotype associated with a traffic stop light whose arc width for that rotating red animated dynamic optotype is approximately 135 cm in diameter giving a typical 20/20 visual perception distance of 200 feet. An individual that was typically less than 200 feet would be able to detect the rotation of the image while an individual with 20/20 visual perception that was further than 200 feet would not be able to detect that rotation.

Item 1—An animated dynamic optotype of a specific arc width diameter whose rotation will be visible to the subject with 20/20 visual acuity at less than a specific distance.

Item 2—The arc width range of visibility of the animated dynamic optotype.

Item 3—Viewing subject

Aspects of the technology described herein include:

1. A method for measuring acuity using rotating animated dynamic optotype images for infants and children and non-verbal individuals.

2. A method for measuring acuity in color using rotating animated dynamic optotype images for infants and children and non-verbal individuals.

3. A method for measuring acuity using rotating animated dynamic optotype images for individuals with dyslexia and other reading related disorders.

4. A method for measuring acuity in color using rotating animated dynamic optotype images for individuals with dyslexia and other reading related disorders.

5. A method as a screening test using colored rotating animated dynamic optotype images for individuals with dyslexia and other reading related disorders.

6. A method for measuring the peripheral acuity range using rotating animated dynamic optotype images.

7. A method for measuring the peripheral acuity field using rotating animated dynamic optotype images.

8. A method for measuring the changes in the visual field using rotating animated dynamic optotype images that may be indicative of mental function and comprehension.

9. A method for measuring distance perception using rotating animated dynamic optotype images.

10. A method for warning of distance proximity using rotating animated dynamic optotype images.

Although this technology has been illustrated and described herein with reference to preferred embodiments and specific examples thereof, it will be readily apparent to those of ordinary skill in the art that other embodiments and examples can perform similar functions and/or achieve like results. All such equivalent embodiments and examples are within the spirit and scope of the technology described herein and are intended to be covered by the following claims.

What is claimed is:

1. A vision test comprising:
a display surface containing at least one uniformly rotating (non-static) animated dynamic optotype whose calibrated angular arc width, angular rotation speed, rotation direction, segments, gaps, color, background contrast, and stroke-width thickness and incidence of the segment and gaps can be used to determine visual acuity, and used as a quantitative basis for calculating visual refractions;
wherein acuity is determined based upon detection of the angular rotation of the dynamic optotype image; and
wherein that rotation detection threshold becomes a direct measure of acuity as a function of the image attributes and the viewing distance.

* * * * *